US012564516B2

(12) United States Patent
Hallen

(10) Patent No.: US 12,564,516 B2
(45) Date of Patent: Mar. 3, 2026

(54) PROBE FOR LASER ABLATION, ILLUMINATION, AND VISCOELASTIC INJECTION

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 308 days.

(21) Appl. No.: 18/055,691

(22) Filed: Nov. 15, 2022

(65) Prior Publication Data

US 2023/0165714 A1     Jun. 1, 2023

Related U.S. Application Data

(60) Provisional application No. 63/264,750, filed on Dec. 1, 2021.

(51) Int. Cl.
| | |
|---|---|
| *A61F 9/008* | (2006.01) |
| *A61B 18/20* | (2006.01) |
| *A61B 18/22* | (2006.01) |
| *A61B 90/30* | (2016.01) |

(52) U.S. Cl.
CPC .. *A61F 9/00802* (2013.01); *A61B 2018/2005* (2013.01); *A61B 2018/2211* (2013.01); *A61B 2090/306* (2016.02); *A61F 2009/00868* (2013.01); *A61F 2009/00891* (2013.01)

(58) Field of Classification Search
None
See application file for complete search history.

(56) References Cited

U.S. PATENT DOCUMENTS

| | | | | |
|---|---|---|---|---|
| 4,583,539 | A | 4/1986 | Karlin et al. | |
| 4,846,172 | A | 7/1989 | Berlin | |
| 5,588,952 | A * | 12/1996 | Dandolu | A61M 1/84 |
| | | | | 604/27 |
| 6,013,073 | A * | 1/2000 | Choukroun | A61B 17/00008 |
| | | | | 606/15 |
| 9,561,078 | B2 * | 2/2017 | Seibel | A61B 1/0017 |
| 9,820,883 | B2 * | 11/2017 | Berlin | A61F 9/00781 |
| 11,071,647 | B2 * | 7/2021 | Berlin | G02B 23/2423 |
| 11,622,885 | B2 * | 4/2023 | Meckel | A61F 9/00736 |
| | | | | 600/249 |
| 11,844,725 | B2 * | 12/2023 | Chon | A61F 9/00763 |
| 11,877,956 | B2 * | 1/2024 | Charles | A61F 9/00727 |
| 2010/0280317 | A1 * | 11/2010 | Silvestrini | A61B 1/0646 |
| | | | | 600/109 |

(Continued)

FOREIGN PATENT DOCUMENTS

WO         0189437 A2     11/2001

*Primary Examiner* — Shirley X Jian

(57) ABSTRACT

Microsurgical instruments having combined illumination, laser ablation, and viscoelastic injection functions. A surgical instrument includes a probe having a main lumen and a port at a distal end thereof. The probe may further include one or more optical fibers within the main lumen, the optical fibers configured to project laser light and illumination light. Laser light may be emitted from the distal end of the probe for disrupting an ocular tissue, while illumination light may be simultaneously emitted, axially or laterally, to provide enhanced visualization of the intraocular space during tissue disruptance. Upon disrupting the tissue, a viscoelastic fluid may be injected from the port to maintain an integrity of the intraocular space.

15 Claims, 9 Drawing Sheets

(56)     References Cited

U.S. PATENT DOCUMENTS

| | | | | |
|---|---|---|---|---|
| 2015/0231287 A1* | 8/2015 | Lin | .................. | A61M 25/0097 |
| | | | | 607/80 |
| 2019/0201238 A1* | 7/2019 | Bacher | ................... | A61F 9/008 |
| 2020/0330281 A1* | 10/2020 | Junger | ................. | H01S 3/2253 |
| 2021/0113819 A1* | 4/2021 | Kalorin | ................ | A61M 25/10 |
| 2021/0145642 A1* | 5/2021 | Berlin | ...................... | A61F 2/14 |
| 2021/0173143 A1* | 6/2021 | Diao | ................. | G02B 6/02319 |
| 2021/0290438 A1* | 9/2021 | Hallen | ............... | A61F 9/00836 |
| 2022/0280343 A1* | 9/2022 | Junger | ............... | A61F 9/00802 |
| 2023/0248434 A1* | 8/2023 | Altshuler | .......... | A61B 1/00091 |
| | | | | 600/108 |

* cited by examiner

100

260 220 210 106 104 132 212 130 250

134   110   118

114   108   128

116   126   112   134

102

122   120

124

PROBE FOR LASER ABLATION, ILLUMINATION, AND VISCOELASTIC INJECTION

FIELD

Embodiments of the present disclosure generally relate to small-gauge instrumentation for surgical procedures, and more particularly, to small-gauge instrumentation for glaucoma surgery.

BACKGROUND

Glaucoma is a group of eye disorders that damage the optic nerve (the bundle of nerve fibers that carries information from the eye to the brain), which can lead to severe vision loss or complete blindness. In fact, glaucoma is the leading cause of irreversible blindness in the world, and affects nearly 80 million people worldwide.

Glaucoma is often characterized by an elevation in eye pressure, known as intraocular pressure, which is caused by a resistance to drainage of the aqueous humor from the eye. The aqueous humor is a clear fluid produced by the eye to provide nutrition to the many structures thereof, as well as to maintain the eye in a pressurized state. The aqueous humor typically flows from the ciliary body into the anterior chamber, out through a spongy tissue near the front of the eye called the trabecular meshwork, and into a drainage structure called Schlemm's canal. From there, the aqueous humor empties into collector channels, then to the veins, and eventually back into the body's circulatory system. In many forms of glaucoma, the aqueous humor does not flow freely through the trabecular meshwork, which causes an increase in intraocular pressure, leading to damage to the optic nerve and vision loss.

Currently, glaucoma and pre-glaucoma are treated by reducing intraocular pressure using one or more modalities, including medication and various forms of glaucoma surgery, such as minimally invasive glaucoma surgery (MIGS). Surgical procedures for glaucoma generally involve the mechanical disruption of the trabecular meshwork and/or Schlemm's canal to form a pathway for outflow of the aqueous humor, i.e., a uveoscleral channel known as a "fistula." Examples of such techniques include trabeculectomy, trabeculotomy, and goniotomy. During such procedures, upon formation of the fistula, a viscoelastic material may be injected into the trabecular meshwork and/or Schlemm's canal to engorge and/or maintain the fistula, as well as the integrity of the anterior chamber of the eye.

The disruption of the trabecular meshwork and/or Schlemm's canal, as well as the injection of the viscoelastic material, may each be performed by a surgeon using distinct microsurgical instruments inserted through one or more incisions made in the eye. In certain instances, a separate incision may be provided for each microsurgical instrument when using multiple instruments simultaneously. The microsurgical instruments typically utilized during a glaucoma surgery include a mechanical trabeculotomy/goniotomy probe with cutting blades for severing tissues, as well as a viscoelastic injection device, e.g., a syringe. During some procedures, an illuminator is also used, as proper illumination of the trabecular meshwork and/or Schlemm's canal is advantageous for purposes of disruption thereof with the trabeculotomy/goniotomy probe. Thus, during any given glaucoma surgical procedure, two or more microsurgical instruments may be used, adding unnecessary complexity to the procedure.

Further, the utilization of conventional trabeculotomy/goniotomy probes may result in inconsistent results between glaucoma procedures, as fistula size and therefore, procedural effectiveness, may be surgeon-dependent when utilizing mechanical cutting blades. Such probes may also pose safety concerns, as mechanical cutting blades may cause unwanted damage to tissues surrounding a surgical site to be disrupted thereby.

Accordingly, what is needed in the art are improved methods and apparatus for glaucoma surgery.

SUMMARY

The present disclosure generally relates to microsurgical instruments for ophthalmic surgical procedures, and more particularly, microsurgical instruments having combined laser ablation, illumination, and viscoelastic injection functions.

In certain embodiments, a surgical instrument for an ophthalmic procedure is provided. The surgical instrument comprises: a handle; a probe coupled to the handle, the probe comprising: a tube; a first port formed proximate to a distal end of the tube for injecting a fluid into an intraocular space; an optically clear or transparent window disposed within the distal end of the tube; and one or more optical fibers extending at least partially through the tube, the optical fibers transmitting a laser light for irradiating an area proximate to the window for ablation of an ocular tissue, the one or more optical fibers further transmitting an illumination light for illumination of the intraocular space of a patient.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to microsurgical instruments for ophthalmic surgical procedures, and more particularly, microsurgical instruments having combined laser ablation, illumination, and viscoelastic injection functions.

In certain embodiments, a surgical instrument includes a base and a probe having a main lumen and a port at a distal tip thereof. In certain embodiments, the probe may further include a single optical fiber within the main lumen, the single optical fiber configured to project both laser light and illumination light. According to certain embodiments, laser light may be emitted from a distal end of the optical fiber and through a window at the distal tip of the probe, the laser light for disrupting an ocular tissue, e.g., the trabecular meshwork. Simultaneously, illumination light may be emitted, axially or laterally, from the optical fiber to provide enhanced visualization of the intraocular space during disruptance of the trabecular meshwork. In certain other embodiments, separate optical fibers may be used for projecting laser and illumination light. For example, in such embodiments, a first optical fiber may be used for projecting laser light while one or more additional optical fibers may be used to project illumination light. In further embodiments, upon disrupting the trabecular meshwork with the laser light, a viscoelastic material may be injected from the port of the probe into the disrupted trabecular meshwork in order to maintain an integrity of the intraocular space.

Figure 1B:
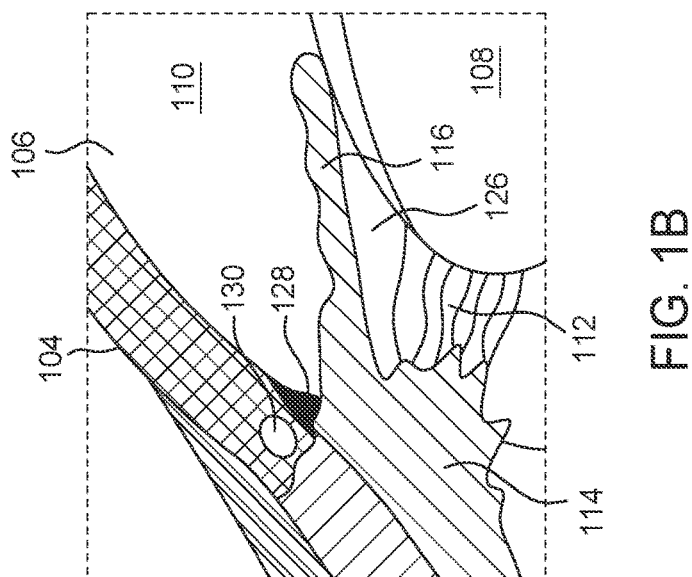
FIG. 1B illustrates an enlarged cross-sectional view of a portion of the eye of FIG. 1A.
Figure 1A:
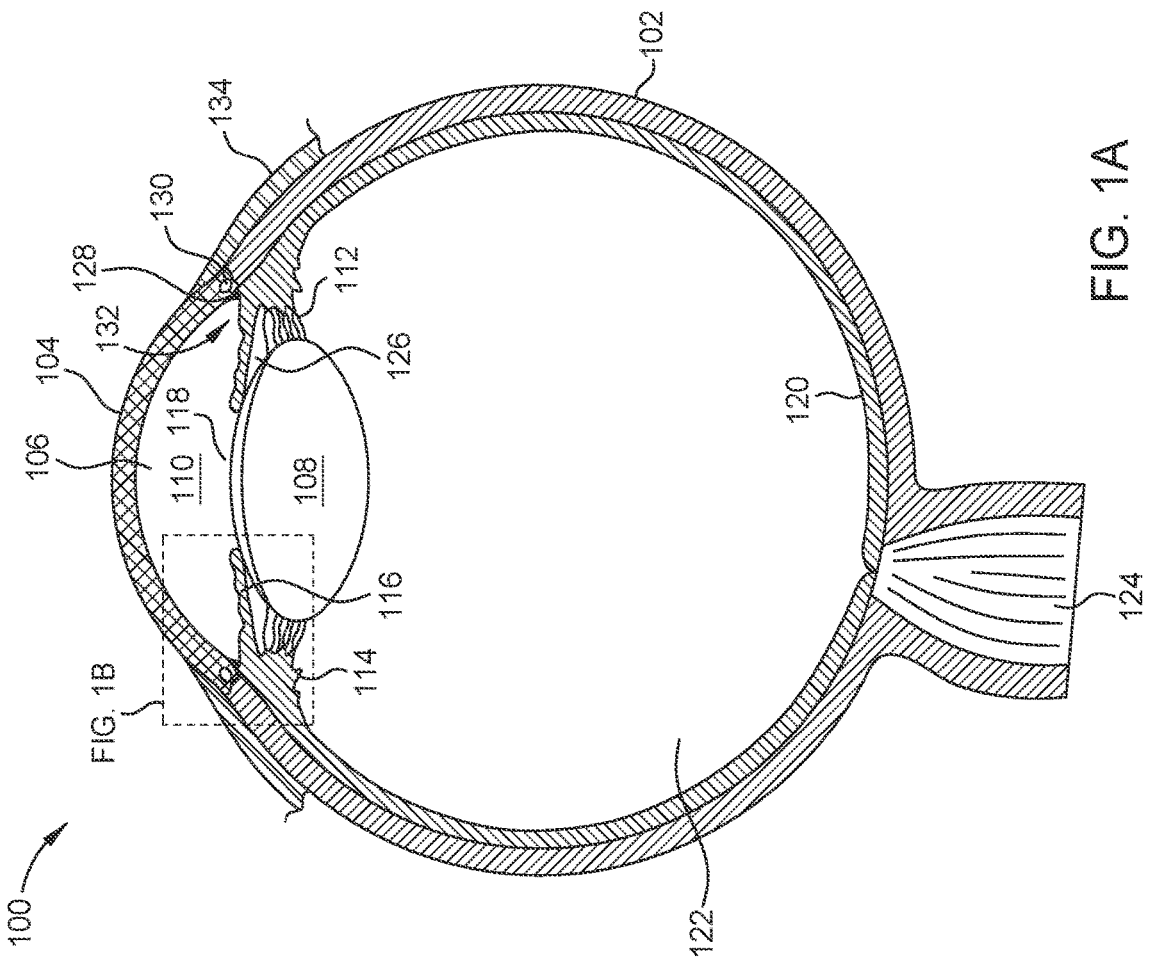
FIG. 1A illustrates a cross-sectional view of an eye and the interior anatomical structure thereof.

FIGS. 1A-1B depict schematic cross-sectional views of eye 100 to illustrate an anatomy of the eye. As shown, the outer layer of eye 100 includes sclera 102, which serves as a supporting structure for eye 100. Sclera is connected to conjunctiva 134, a thin membrane that that lines the eyelid (not shown) and loops back to cover sclera 102 and provide protection thereto. The front of sclera 102 includes cornea 104, which is a transparent tissue that enables light to enter eye 100. Anterior chamber 106 is located between cornea 104 and crystalline lens 108. Anterior chamber 106 contains a clear fluid called aqueous humor 110, which helps maintain the shape of eye 100 and provides nourishment for, e.g. cornea 104. Crystalline lens 108 is positioned in eye 100 via zonular fibers 112, which couple to ciliary body 114. Within anterior chamber 106, iris 116 encircles an outer perimeter of lens 108 and forms pupil 118 at its center. The diameter of pupil 118 controls the amount of light passing through lens 108 to retina 120, which is a thin layer of tissue disposed at the back of vitreous chamber 122. Retina 120 receives the light that lens 108 has focused and converts the light into neural signals which are sent, via optic nerve 124, to the brain for visual recognition. A posterior chamber 126 is located between iris 116 and lens 108.

As shown in FIG. 1B, the anatomy of eye 100 further includes trabecular meshwork 128, which is a narrow band of tissue within eye 100 that encircles iris 116 near iridocorneal angle 132, where iris 116 and cornea 104 meet. Trabecular meshwork 128 is a spongy tissue formed of various fibrous layers having micron-sized pores that enable aqueous humor 110 to drain from anterior chamber 106 into an annular channel called Schlemm's canal 130, before eventually being drained into the blood system. Because aqueous humor 110 is constantly being produced by eye 100, any obstruction in trabecular meshwork 128 preventing aqueous humor 110 from escaping anterior chamber 106 results in elevation of intraocular pressure within eye 100. The elevated intraocular pressure may lead to damage of the optic nerve, and ultimately, vision loss or blindness.

Figure 2A:
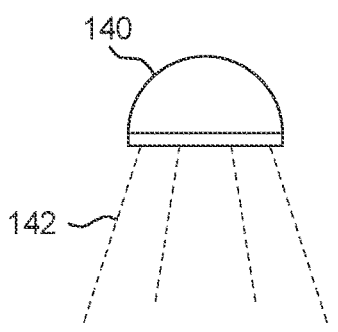
FIG. 2A illustrates a portion of a prior art surgical instrument disposed within an eye of a patient during a glaucoma surgery, according to certain embodiments of the present disclosure.
Figure 2B:
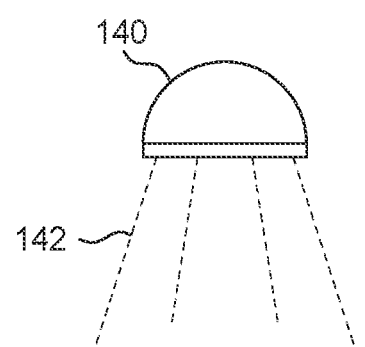
FIG. 2B illustrates a portion of a prior art surgical instrument disposed within an eye of a patient during a glaucoma surgery, according to certain embodiments of the present disclosure.

FIGS. 2A-2B illustrate a side sectional view of the interior anatomy of eye 100 during the performance of glaucoma surgery, e.g., a goniotomy procedure to eliminate an obstructed trabecular meshwork or Schlemm's canal, using a prior art surgical instrument 200 having probe 212, and conventional injection device 250. In the example of FIGS. 2A-2B, probe 210 is a mechanical cutting device, e.g., a goniotomy knife with mechanical blades, while injection device 250 may be a syringe and needle or an injector coupled to, e.g., a pneumatic line. Furthermore, illumination light 142 is provided by a source 140 external to eye 100, such as an ophthalmic operating microscope. However, in certain cases, an illumination probe, e.g., an endoilluminator, may be inserted into eye 100 simultaneously with probe 210.

As shown FIG. 2A, probe 210 is inserted into anterior chamber 106 through a small, self-sealing incision 212 made in cornea 104 with, e.g., a surgical blade or the like. Distal end 202 of probe 210 is advanced through anterior chamber 106 until it contacts or is substantially adjacent to trabecular meshwork 128 at iridocorneal angle 132. Trabecular meshwork 128 is then disrupted by probe 210 to form a fistula 220, which may pass through trabecular meshwork 128 toward Schlemm's canal 130. Formation of fistula 220 enables improved outflow of aqueous humor 110 from anterior chamber 106 into Schlemm's canal 130, which in cases of glaucoma or pre-glaucoma, may relieve intraocular pressure within eye 100 caused by, e.g., an obstructed trabecular meshwork. In certain instances, a plurality of fistulas 220 are formed through trabecular meshwork 128 around a circumference of iridocorneal angle 132 to further improve outflow of aqueous humor 110. In certain instances, aqueous humor 110 may then flow into an artificially created reservoir called a bleb (not shown) under conjunctiva 134.

In FIG. 2B, injection device 250 has been inserted into eye 100 through the same (and thus requiring removal of probe 210) or different incision 212 as probe 210. A distal tip 252 of injection device 250 is advanced through anterior chamber 106 until it is substantially adjacent to or within the formed fistula 220. Viscoelastic fluid 260 is then injected from injection device 250 into fistula 220 within trabecular meshwork 128 to engorge and/or maintain (e.g., keep open) fistula 220, as well as to maintain anterior chamber 106, and facilitate outflow of aqueous humor 110 from anterior chamber 106 into Schlemm's canal 130. Thus, in the example of FIGS. 2A-2B, two or more microsurgical instruments are inserted and utilized, either simultaneously or in sequence, during the glaucoma surgical procedure, creating unnecessary complexity to the procedure.

Figure 3:
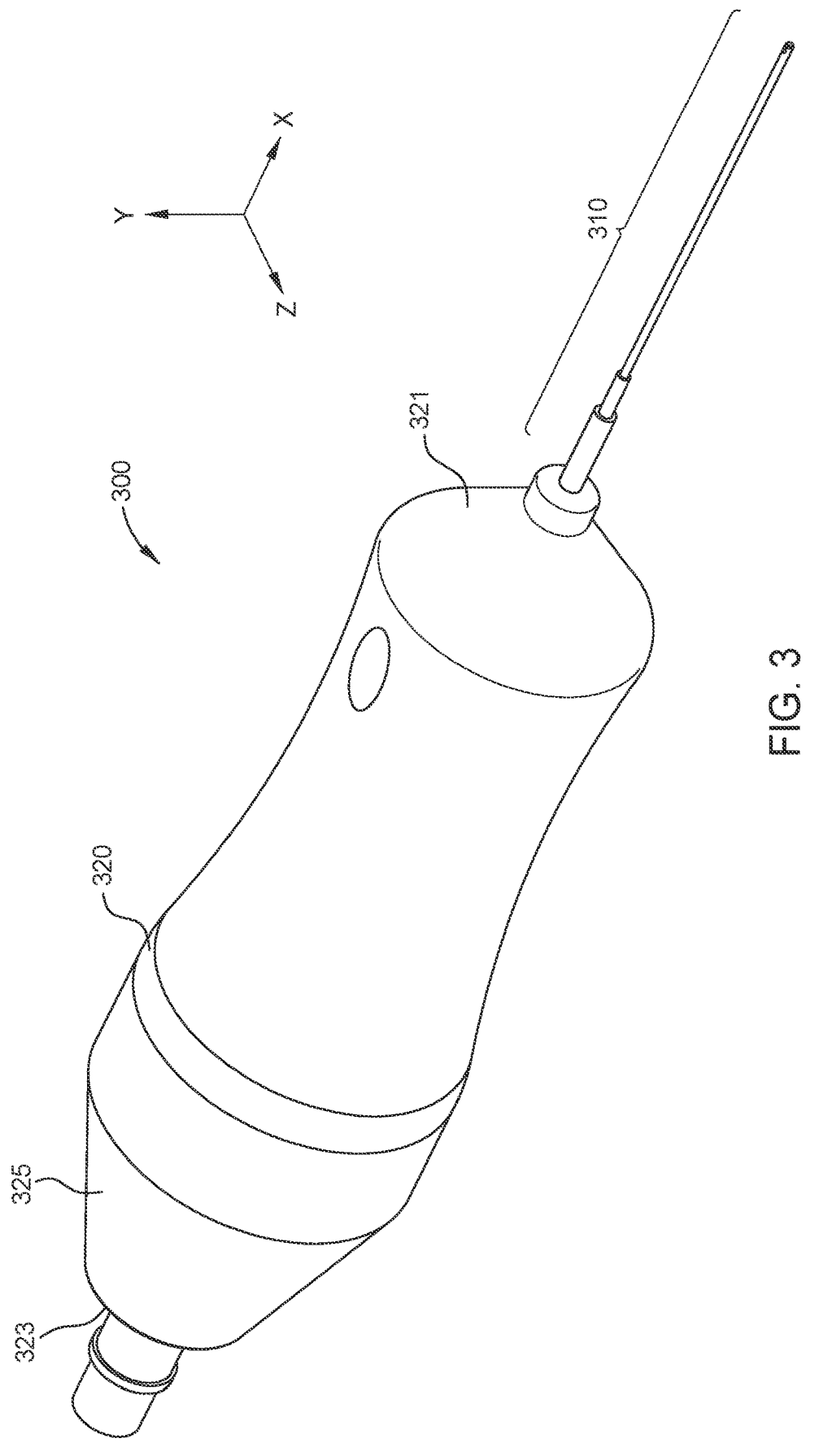
FIG. 3 illustrates a perspective view of an example surgical instrument, according to certain embodiments of the present disclosure.

FIG. 3 illustrates a perspective view of an improved surgical instrument 300, according to certain embodiments described herein. As depicted in FIG. 3, surgical instrument 300 comprises probe 310 and base unit 320. Probe 310 is partially and longitudinally disposed through distal end 321 of base unit 320 and may be directly or indirectly attached thereto within an interior chamber of base unit 320. Note that, as described herein, a distal end or portion of a component refers to the end or the portion that is closer to a patient's body during use thereof. On the other hand, a proximal end or portion of the component refers to the end or the portion that is distanced further away from the patient's body.

In certain embodiments, base unit 320 is a hand piece having an outer surface configured to be held by a user, such as a surgeon. For example, base unit 320 may be ergonomically contoured to substantially fit the hand of the user. In certain embodiments, the outer surface may be textured or have one or more gripping features formed thereon, such as one or more grooves and/or ridges. Base unit 320 may be made from any materials commonly used for such instruments and suitable for ophthalmic surgery. For example, base unit 320 may be formed of a lightweight aluminum, a polymer, or other suitable material. In some embodiments, base unit 320 may be sterilized and used in more than one surgical procedure, or may be a single-use device.

Base unit 320 further provides a plurality of ports 323 (although only one port 323 is depicted in FIG. 3) at proximal end 325 thereof for supply lines to be routed into an interior chamber of base unit 320. For example, port 323 may provide a connection between base unit 320 and a supply line of a viscoelastic source (not shown) for viscoelastic injection. Port 323 may also provide a connection to an optical fiber cable that couples to light sources for providing laser light as well as illumination light.

Figure 4A:
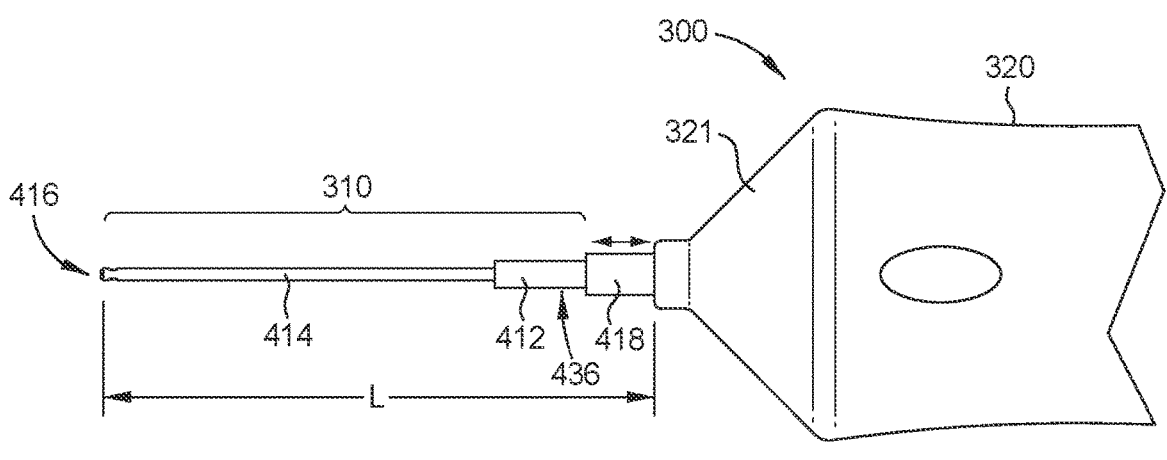
FIG. 4A illustrates a plan view of a portion of the surgical instrument of FIG. 3, according to certain embodiments of the present disclosure.

FIG. 4A illustrates a plan view of probe 310 and distal end 321 of base unit 320. As shown, probe 310 may be an elongated laser ablation member that may be inserted into an eye, e.g., through an insertion cannula and/or incision, for performing a glaucoma surgical procedure, such as goniotomy, trabeculotomy, or trabeculectomy. Probe 310 may thus be formed of materials suitable for minimally invasive glaucoma surgeries (MIGS). In certain embodiments, probe 310 includes one or more sections that are formed of materials configured to transmit laser light, visible light, ultraviolet light, infrared light, or any other type of light. For example, probe 310 may include one or more sections formed of a translucent or transparent material, such as a plastic and/or polymeric material. Probe 310 may further include one or more sections formed of more conventional surgical-grade materials, such as stainless steel and/or aluminum.

In certain embodiments, probe 310 has a length L between about 15 mm and about 30 mm, but may have a larger or smaller length in some embodiments. In certain embodiments, probe 310 may comprise a hollow cylindrical (e.g., non-segmented) tube having an outer diameter less than about 20 gauge. In some embodiments, probe 310 is segmented into two or more portions (e.g., regions or segments) having outer diameters of differing sizes. For example, as shown in FIG. 4A, probe 310 may include proximal portion 412 having a larger outer diameter than distal portion 414, which terminates at distal tip 416. In certain embodiments, proximal portion 412 has an outer diameter of about 23 gauge and distal portion 414 has an outer diameter of about 25 gauge. In some embodiments, proximal portion 412 has an outer diameter of about 25 gauge and distal portion 414 has an outer diameter of about 27 gauge. In some other embodiments, proximal portion 412 has an outer diameter of about 27 gauge and distal portion 414 has an outer diameter of about 29 gauge. In further embodiments, a medial portion (not shown) is disposed between proximal portion 412 and distal portion 414, and has an outer diameter lesser than that of proximal portion 412 and greater than that of distal portion 414.

In certain embodiments, surgical instrument 300 further includes stiffener 418 fixedly or slidably coupled to and substantially surrounding at least a portion of probe 310. For example, stiffener 418 may be slidably coupled to an exterior surface 436 of the proximal portion 412 of probe 310 and may extend from and retract into base unit 320. Stiffener 418 may be adjustable relative to probe 310, enabling a user to position stiffener 418 at different points along length L of probe 310 exterior to base unit 320. Accordingly, a user may selectively adjust the level of stiffness of probe 310 by re-positioning stiffener 418 relative to distal tip 416, thereby manipulating the amount of support provided to probe 310 and stabilizing surgical instrument 300 during use thereof.

Figure 4B:
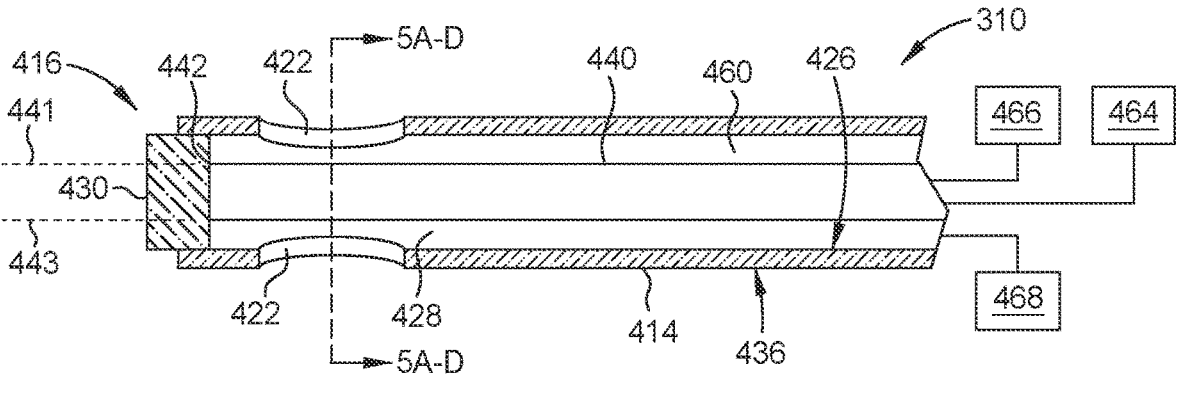
FIG. 4B illustrates a stylized longitudinal cross-sectional view of a portion of the surgical instrument of FIG. 3, according to certain embodiments of the present disclosure.
Figure 4C:
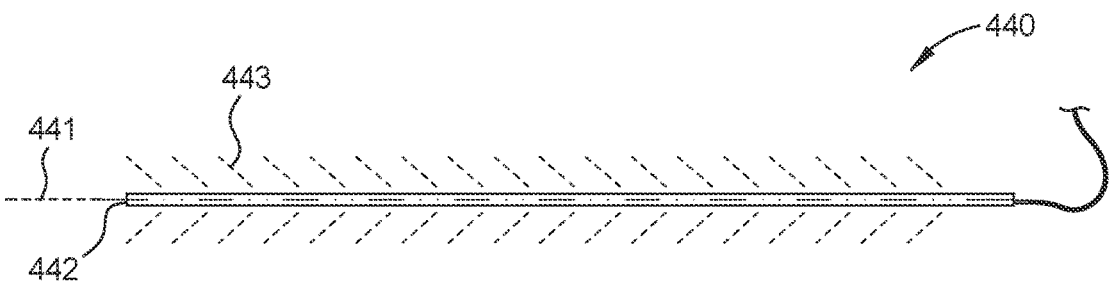
FIG. 4C illustrates a stylized longitudinal cross-sectional view of a portion of the surgical instrument of FIG. 3, according to certain embodiments of the present disclosure.
Figure 5A:
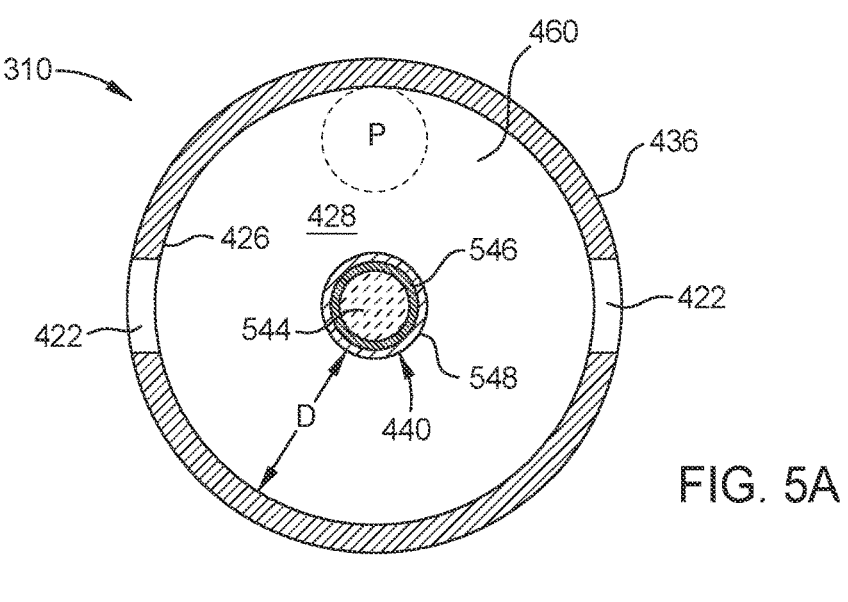
FIG. 5A illustrates a front sectional view of an exemplary surgical instrument, according to certain embodiments of the present disclosure.
Figure 5B:
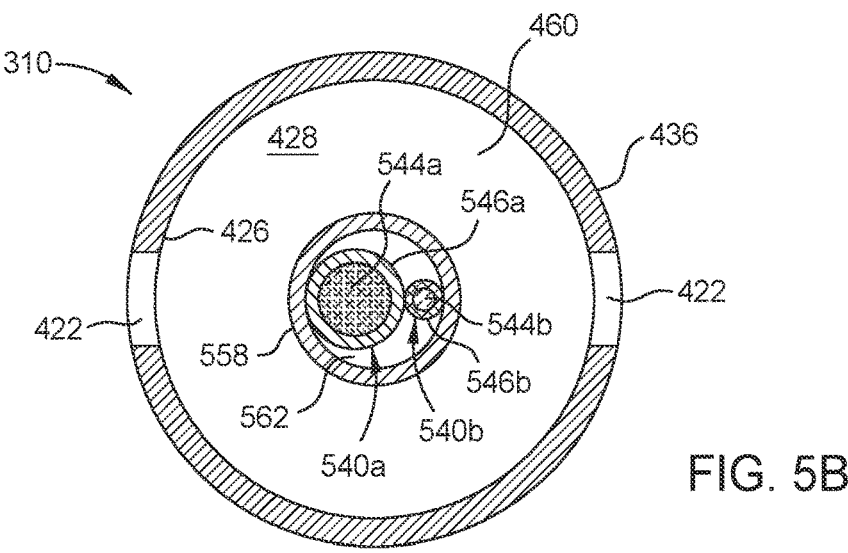
FIG. 5B illustrates a front sectional view of an exemplary surgical instrument, according to certain embodiments of the present disclosure.
Figure 5C:
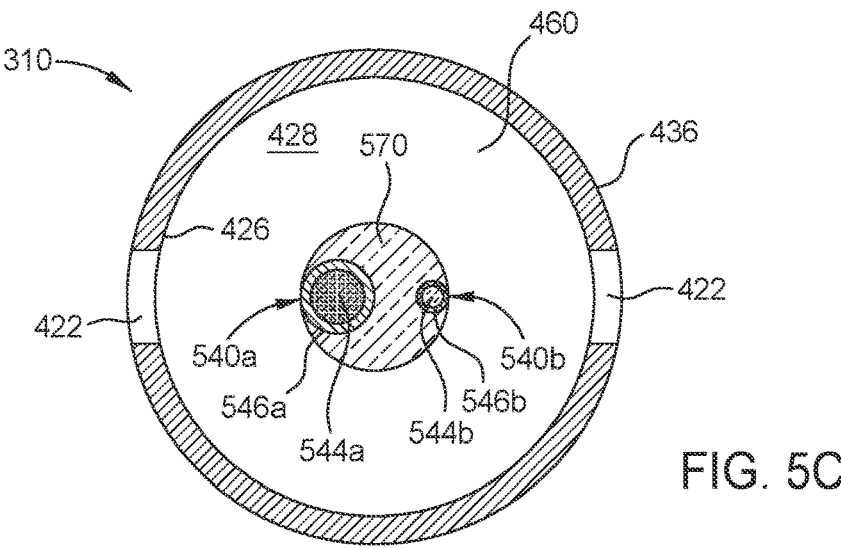
FIG. 5C illustrates a front sectional view of an exemplary surgical instrument, according to certain embodiments of the present disclosure.
Figure 5D:
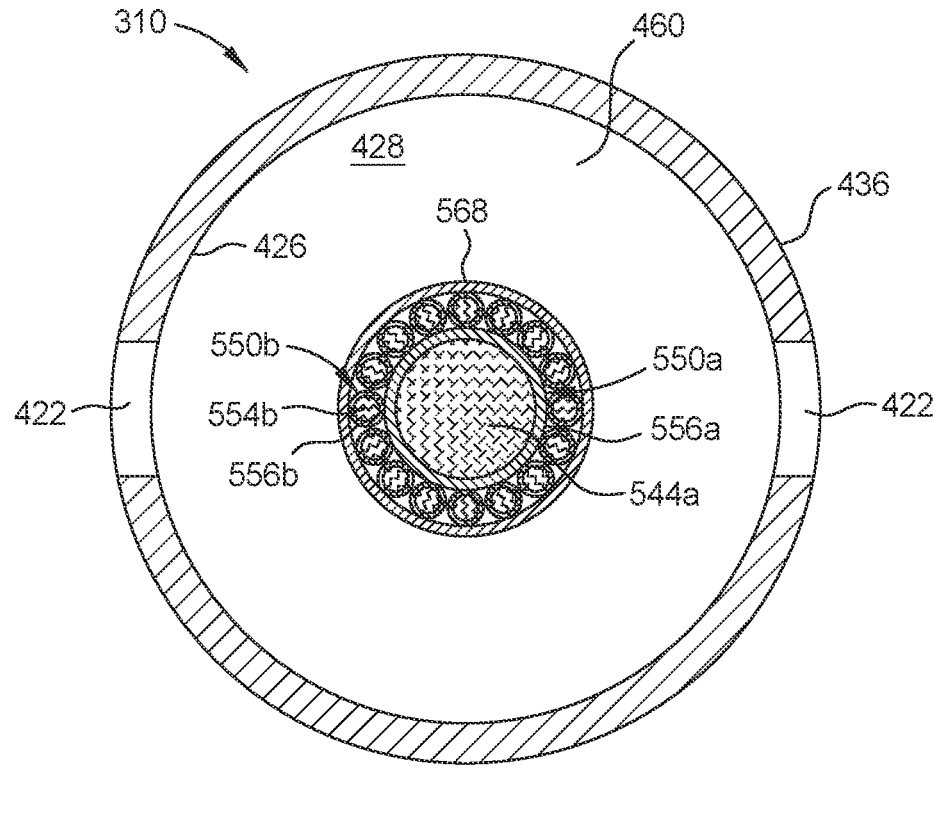
FIG. 5D illustrates a front sectional view of an exemplary surgical instrument, according to certain embodiments of the present disclosure.

As described above, in certain embodiments, surgical instrument 300 provides a single optical fiber that is configured to project both laser light as well as illumination light. Various examples of using a single optical fiber for projecting both laser light and illumination light are depicted in FIGS. 4B-4C and 5A. In certain other embodiments, one or more optical fibers may be used for projecting laser light while one or more additional optical fibers may be used for projecting illumination light. Various examples of using multiple fibers for projecting laser light and illumination light are depicted in FIGS. 5B-5D.

FIGS. 4B-4C illustrate stylized longitudinal cross-sectional views of distal portion 414 of probe 310 having optical fiber 440 housed therein. As depicted, probe 310 includes main lumen 460 and one or more ports 422 near distal tip 416, which has a protective window 430 placed therein. In certain embodiments, main lumen 460 has at least a substantially circular cross-section, shown in FIGS. 5A-5D. However, other morphologies for the cross-section of main lumen 460, such as polygonal or oval-like, are contemplated. In the example shown in FIG. 4B, two substantially circular ports 422 are depicted on opposing sides of main lumen 460 in distal portion 414. Ports 422 are sized and shaped to allow viscoelastic to be injected from main lumen 406 to an exterior of probe 310 during glaucoma surgery. However, any number, location, and shape for ports 422 is contemplated. Furthermore, although described with reference to viscoelastic fluids, probe 310 may be utilized to inject other fluids during ophthalmic surgical procedures, including infusion fluids and the like. Viscoelastic, or other suitable fluids, may be supplied to lumen 406 by fluid source 468, which is coupled to probe 310 at, e.g., port 323, by a supply line (not shown). While using probe 310, a user may initiate flow of viscoelastic from fluid source 468, into lumen 406, and out from ports 422 to a surgical site via activation of one or more toggles (e.g., buttons, switches, etc.) on base unit 320, a surgical console in communication with probe 310 (not shown), or a foot pedal in communication with a surgical console and/or probe 310 (not shown).

Optical fiber 440 may be designed to operate as an optical waveguide and propagate laser light 441 through a terminal end 442 thereof. The characteristics of laser light 441 propagated through optical fiber 440 are such that laser light 441 causes disruption of trabecular meshwork and/or Schlemm's canal fibers within the path of laser light 441. Disruption refers to the breaking down of the tissue by rapid ionization of molecules thereof. In some examples, laser light 441 may be produced by laser light source 464 optically coupled to optical fiber 440 using an optical fiber cable, as described above. In some embodiments, laser light 441 propagated by optical fiber 440 is an ultraviolet ("UV") (<350 nm) laser light. In other embodiments, laser light 441 is an argon blue-green laser light (488 nm), a Nd-YAG laser light (532 nm) such as a frequency-doubled Nd-YAG laser light, a krypton red laser light (647 nm), a diode laser light (805-810 nm), or any other suitable type of laser light for ophthalmic surgery.

In some embodiments, laser light source 464 may produce laser light 441 having a pulse rate within a range of about 1 kilohertz (kHz) and about 500 kHz. This range can effectively provide disruption of the trabecular meshwork and/or Schlemm's canal. Other pulse rate ranges can also provide disruption and are thus contemplated as well. In some examples, laser light source 464 produces a picosecond or femtosecond laser light 441. In some embodiments, laser light source 464 may produce a continuous coherent laser light 441. For example, laser light source 464 may produce a continuous coherent laser light 441 at low power. While using probe 310, a user may initiate propagation of laser light 441 from laser light source 464, through probe 310, and to a surgical site via activation of one or more toggles (e.g., buttons, switches, etc.) on base unit 320, a surgical console in communication with probe 310 (not shown), or a foot pedal in communication with a surgical console and/or probe 310 (not shown), similar to activating viscoelastic injection.

In certain embodiments, optical fiber 440 is disposed within main lumen 460 and terminates at terminal end 442 disposed against or adjacent to window 430 such that laser light 441 projecting from optical fiber 440 will be projected distally through window 430 with sufficient power to sever trabecular mesh and/or Schlemm's canal fibers disposed distal to window 430. Accordingly, window 430 comprises an optically clear or transparent material. Examples of the transparent material include sapphire, fused silica, or other glass or ceramics materials with high transition temperatures. In certain aspects, the transparent material has optical power and, in certain other aspects, the transparent material does not have optical power. Optical power (also referred to as dioptric power, refractive power, focusing power, or convergence power) is the degree to which a lens, mirror, or other optical system converges or diverges light. Accordingly, window 430 may itself be a lens, such as a spherical lens having concave or convex surfaces, or a nonspherical lens.

In the embodiment depicted in FIG. 4B, optical fiber 440 is rigidly suspended within main lumen 460 such that optical fiber 440 is separated from interior sidewall 426 of probe 310 and optical fiber 440 is circumferentially surrounded by space 428. Space 428 formed between optical fiber 440 and interior sidewall 426 of probe 310 provides a coaxial path for distal flow of viscoelastic through probe 310. In certain embodiments, optical fiber 440 may be centrally disposed within main lumen 460 such that a radial distance between interior sidewall 426 and the optical fiber 440 is uniform along a circumference of optical fiber 440. In certain embodiments, however, optical fiber 440 may be disposed along (e.g., coupled to) interior sidewall 426 (not shown). For example, optical fiber 440 may be coupled to interior sidewall 426 along a longitudinal length thereof, extending between ports 422. Optical fiber 440 may be coupled to interior sidewall 426 with any suitable adhesive or bonding mechanism, such as an epoxy or acrylic adhesive.

In the embodiments of FIGS. 4B-4C, optical fiber 440 is further configured to propagate illumination light 443 in addition to and separate from laser light 441. For example, illumination light source 466 may be used to provide illumination light 443 to the optical fiber 440 in a continuous or pulsed manner. Optical fiber 440 propagates illumination light 443 in one of a variety of ways to illuminate the intraocular space, e.g., anterior chamber. An example of illumination light source 466 includes a UV light source, a violet light source, a blue light source, a white light source, an infrared ("IR") or near IR light source, or any other suitable type of illumination light source. For example, an LED-based illumination light source 466 may be utilized. In further examples, a xenon-or halogen-based illumination light source 466 may be utilized. While using probe 310, a user may initiate propagation of illumination light 443 from illumination light source 466, through probe 310, and to a surgical site via activation of one or more toggles (e.g., buttons, switches, etc.) on base unit 320, a surgical console in communication with probe 310 (not shown), or a foot pedal in communication with a surgical console and/or probe 310 (not shown), similar to activating viscoelastic injection and/or laser light 441 propagation.

In embodiments where a single optical fiber 440 is used for projecting both laser light as well as illumination light, laser light source 464 may be configured to focus laser light 441 on a core of optical fiber 440 and thus, laser light 441 is transmitted through the core. In certain embodiments, illumination light source 466 is configured to focus illumination light 443 onto both the core and a cladding of optical fiber 440, in which case both the cladding and the core transmit illumination light 443. In yet some other embodiments, illumination light source 466 is configured to focus illumination light 443 onto just the core or the cladding, in which case only one of the core or the cladding transmit illumination light 443. Thus, optical fiber 440, including a core and a cladding, is capable of transmitting laser light 441 (through the core) and illumination light 43 (through the cladding and the core) in the same fiber. In certain embodiments, single optical fiber 440 may include two or more cores. For example, single optical fiber 440 may be a multi-core fiber (MCF). In such embodiments, laser light 441 and/or illumination light 443 may be propagated through two or more cores of the single optical fiber 440. In certain embodiments, laser light 441 may be propagated through one core and illumination light 443 may be propagated through a different core in optical fiber 440, and therefore optical fiber 440 may include one or more cores through which laser light 441 and illumination light 443 are separately propagated.

In certain embodiments, illumination light 443 is axially projected along with laser light 441 from terminal end 442 of optical fiber 440 (shown in FIG. 4B). In certain embodiments, illumination light 443 is diffusely projected from terminal end 442. In certain embodiments, illumination light 443 undergoes total internal reflection within optical fiber 440, and thus, is only projected from terminal end 442. For example, optical fiber 440 is an end-emitting optical fiber. In certain embodiments, illumination light 443 is not completely reflected within optical fiber 440 and may be emitted through a sidewall of a cladding alternatively or in addition to terminal end 442. For example, optical fiber 440 is an edge-emitting or side-emitting optical fiber, where illumination light 443 is emitted radially outward therefrom (shown in FIG. 4C). Illumination light 443 is propagated simultaneously with laser light 441 or sequentially pulsed with laser light 441. In certain embodiments, propagation of illumination light 443 through optical fiber 440 and into the intraocular space may be modulated by utilizing different types of illumination light sources 466, utilizing different materials for optical fiber 440, modifying the physical arrangement of optical fiber 440 within probe 310, and/or by utilizing different materials for probe 310.

FIG. 4C illustrates an example of optical fiber 440 propagating both laser light 441 and illumination light 443 therefrom. In the example of FIG. 4C, laser light 441 and illumination light 443 are emitted through terminal end 442 of optical fiber 440, while illumination light 243 is also emitted radially outward from optical fiber 440. In the example of FIG. 4C, laser light 441 may be focused onto a core of optical fiber 440 while illumination light 443 is focused onto the core and/or a cladding of optical fiber 440. However, as described above, in certain other embodiments, illumination light 443 may instead be only focused on the core of optical fiber 440. In such embodiments (not shown), illumination light 443 may only be emitted axially through terminal end 442 of optical fiber 440.

In certain embodiments, optical fiber 440 is communicatively coupled to a digital visualization system, such as the NGENUITY® 3D Visualization System produced by Alcon. Other digital visualization systems, including those produced by other manufacturers, are also contemplated for use with the embodiments described herein. Utilization of a digital visualization system may enable modification of the color and intensity of illumination light 443 emitted from optical fiber 440 by adjustment of hue, saturation, gamma, tint, and/or other light parameters.

In certain embodiments, optical fiber 440 has a diameter between about 20 μm and about 120 μm, such as a diameter between about 40 μm and about 100 μm. For example, optical fiber 440 has a diameter between about 50 μm and about 80 μm. However, smaller or larger diameters are also contemplated. In some embodiments, a light sleeve assembly containing a plurality of optical fibers 440 is utilized. For example, a light sleeve containing a plurality of optical fibers 440 having uniform or different diameters may be utilized. In further embodiments, optical fiber 440 is a multi-mode end-emitting fiber, a single-mode end-emitting fiber, or the like.

FIGS. 5A-5D illustrate exemplary front sectional views of probe 310 of FIGS. 4A-4C, having optical fiber 440 housed therein for projecting both laser and illumination lights. As depicted, probe 310 has a circular cross-section defined by interior sidewall 426 and exterior surface 436. Generally, optical fiber 440 includes core 544 and cladding 546 circumferentially surrounding core 544 in accordance with embodiments of the present disclosure. Core 544 may comprise any transparent material, such as fused silica or glass. In some embodiments, core 544 is doped. For example, core 544 may be germanium-doped silica. Doping core 544 with germanium or a similar dopant may increase the refractive index of core 544 compared to that of the material of cladding 546, hence enabling laser and light guiding properties within core 544.

Cladding 546 may also comprise a transparent material, such as fused silica or glass. In some embodiments, cladding 546 is doped in addition to or instead of doping core 544. For example, cladding 546, which may comprise fused silica, is doped with a dopant that reduces the refractive index of cladding 546 relative to that of core 544. Example dopants include fluorine (F), chlorine (Cl), boron (B), or the like. Cladding 546, when doped, has a lower refractive index than core 544, thus enabling light guiding properties within core 544. Although one cladding 546 is depicted in each of FIGS. 5A-5D, optical fiber 440 may further include one or more additional claddings.

In one example, core 544 has a diameter in the range of 5 μm and about 100 μm, such as a diameter between about 20 μm and about 80 μm, such as a diameter of about 75 μm. However, smaller or larger diameters are also contemplated. In one example, cladding 546 has a thickness between about 5 μm and about 50 μm, such as a thickness between about 15 μm and about 40 μm, such as a thickness of about 25 μm. However, smaller or larger thicknesses are also contemplated.

In certain embodiments as depicted in FIG. 5A, optical fiber 440 is disposed within sleeve 548. Sleeve 548 may couple directly or indirectly to an exterior of cladding 546 and circumferentially surround cladding 546 and core 544 of optical fiber 440 therewithin. Sleeve 548 may act as a tubular structure for providing structural support, rigidity, and suspension of optical fiber 440 within main lumen 460 of probe 310. In certain examples, sleeve 548 facilitates a central axial alignment of optical fiber 440 within main lumen 460 such that a radial distance D between an outer surface of sleeve 548 and interior sidewall of probe 310, e.g., interior sidewall 426, is substantially uniform around a circumference of sleeve 548. Similar to core 544 and cladding 546, sleeve 548 may comprise a transparent material such as fused silica and glass. In further embodiments, sleeve 548 is doped with a dopant to manipulate the refractive index of sleeve 548 as desired. Sleeve 548 may have a thickness between about 5 μm and about 50 μm, such as a thickness between about 15 μm and about 40 μm, such as a thickness of about 25 μm. However, smaller or larger thicknesses are also contemplated. In embodiments where sleeve 548 is directly coupled to optical fiber 440, an inner surface of sleeve 548 may have a diameter substantially similar to an outer diameter of optical fiber 440.

Though depicted as being centrally disposed within main lumen 460, in certain embodiments, optical fiber 440 may be disposed against interior sidewall 426 of probe 310, with or without sleeve 548. For example, optical fiber 440 may be coupled to interior sidewall 426 along a longitudinal portion thereof disposed between ports 422, as indicated by exemplary position P in FIG. 5A. Such an arrangement may enable improved flow of, e.g., viscoelastic, through the interior of probe 310. Optical fiber 440 may be coupled or bonded to interior sidewall 426 via any suitable adhesive or bonding mechanism. For example, an exterior surface of cladding 546 or sleeve 548 may be bonded to interior sidewall 426 of probe 310 with an epoxy or acrylic adhesive. However, other suitable adhesives are also contemplated.

FIGS. 5B-5C illustrate exemplary front sectional views of probe 310 having at least two optical fibers 540a, 540b housed therein. Accordingly, first optical fiber 540a may be utilized to propagate a laser light for tissue severance and second optical fiber 540b may be utilized to propagate an illumination light for illumination of an intraocular space. Each of optical fibers 540a, 540b further includes core 544a, 544b and cladding 546a, 546b, respectively. Cores 544a, 444b and claddings 546a, 546b may be formed of any suitable materials for propagation of laser and illumination light beams, respectively. For example, cores 544a, 544b and claddings 546a, 546b may comprise a transparent material such as fused silica or glass, as described above. Cores 544a, 544b and claddings 546a, 546b may further be doped with one or more dopants depending on desired refractive properties for each of optical fibers 540a, 540b.

The dimensions of optical fibers 540a, 540b, including cores 544a, 544b and claddings 546a, 546b, may be substantially similar to the dimensions of optical fiber 440, core 444, and cladding 446 described above. Although depicted as having different dimensions in FIGS. 5B-5C, optical fibers 540a, 540b and cores 544a, 544b and claddings 546a, 546b may have similar or different dimensions to each other.

As depicted in FIG. 5B, optical fibers 540a, 540b are both disposed within secondary lumen 562 of sleeve 558, which itself may be centrally disposed within main lumen 460 or, e.g., disposed against interior sidewall 426 between ports 422. Similar to sleeve 548, sleeve 558 may provide structural support and containment of optical fibers 540a, 540b within main lumen 460 of probe 310. Sleeve 558 may comprise a transparent material such as fused silica and glass. In further embodiments, sleeve 558 is doped with a dopant to manipulate the refractive index of sleeve 558 as desired. Sleeve 558 may have any suitable thickness to provide appropriate support and rigidity to optical fibers 540a, 540b, such as a thickness between about 5 μm and about 50 μm, such as a thickness between about 15 μm and about 40 μm. For example, sleeve 558 may have a thickness of about 25 μm. However, smaller or larger thicknesses are also contemplated. In certain embodiments, a transparent filler material may be used within secondary lumen 562 to prevent movement of optical fibers 540a, 540b within. For example, an adhesive may fill all areas within secondary lumen 562 that are not occupied by optical fibers 540a, 540b. In other embodiments, optical fibers 540a, 540b are disposed within secondary lumen 562 without the utilization of a filler material.

FIG. 5C illustrates an alternative exemplary arrangement of optical fibers 540a, 540b, without the utilization of sleeve 558. As shown, optical fibers 540a, 540b are placed through spacer tube 570 having one or more longitudinal bores 572 drilled therethrough to allow placement of optical fibers 540a, 540b. Spacer tube 570 may act in a substantially similar manner to sleeve 558 and provide structural support, rigidity, and containment of optical fibers 540a, 540b. In certain embodiments, spacer tube 570 is centrally disposed or suspended within main lumen 460. In certain embodiments, however, spacer tube 570 is disposed against interior sidewall 426, between ports 422. Spacer tube 570 may be formed of any suitable transparent materials, including fused silica and/or glass.

FIG. 5D illustrates an exemplary front sectional view of probe 310 having a first optical fiber 550a configured to propagate a laser light and a plurality of second optical fibers 550b surrounding first optical fiber 550a and configured to propagate illumination light. First optical fiber 550a and second optical fibers 550b include cores 554a, 554b and claddings 556a, 556b, respectively. The materials and dimensions for cores 554a, 554b and claddings 556a, 556b may be substantially the same as those of optical fibers 440 and 540 described above. However, as depicted in FIG. 5D, the dimensions of second optical fiber 550b may be smaller than that of first optical fiber 550a to enable a sufficient volume for space 428 within main lumen 460 for flow of viscoelastic or other fluids therethrough.

As shown in FIG. 5D, first optical fiber 550a is circumferentially surrounded by second optical fibers 550b along an outer diameter thereof. In other words, a ring of second optical fibers 550b is disposed around and in contact with cladding 556a of first optical fiber 550a such that a center of core 554a is equidistant or at least substantially equidistant from centers of cores 554b. In further embodiments, an optional sleeve 568 is disposed around the plurality of second optical fibers 550b and configured to tightly hold second optical fibers 550b against first optical fiber 550a. Sleeve 568 may have any suitable thickness and dimensions to ensure that second fibers 550b are tightly packed together and there is no room for second fibers 550b to be loose or move. Although depicted as being centrally suspended within main lumen 460, first optical fiber 550a and surrounding second optical fibers 540b may be disposed in any suitable location within main lumen 460. For example, first optical fiber 550a and surrounding second optical fibers 550b may be coupled to interior sidewall 426 of probe 310 along a longitudinal portion between ports 422.

In addition to utilizing different arrangements of optical fibers within the probe of a surgical instrument, the propagation of illumination light into an operating region (e.g., an intraocular space) may be modified by the utilization of different materials for the probe and/or by use of a mask. For example, the probe may include one or more sections formed of a translucent or transparent material and one or more sections formed of an opaque or semi-opaque material. In some embodiments, a distal portion of the probe is formed of a translucent or transparent material while the proximal portion of the probe is formed of a metal, such as stainless steel or aluminum. In some embodiments, only a distal tip of the probe (including the area around the ports) is formed of a translucent or transparent material, and the remainder of the distal portion and the entirety of the proximal portion are formed of metal. In further embodiments, both the distal portion and a proximal portion of the probe are entirely formed of a translucent or transparent material.

Figures 6A, 6B:
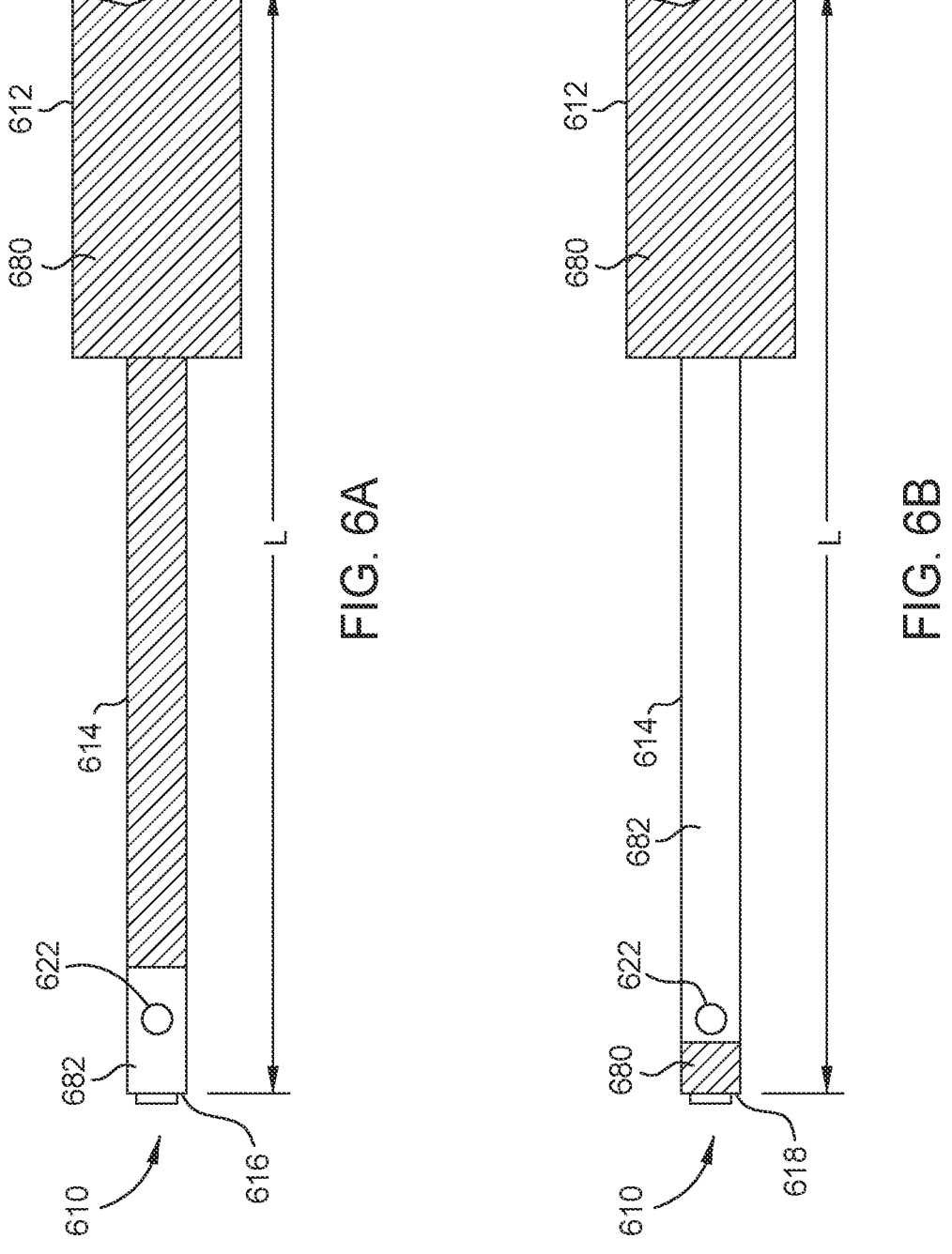
FIG. 6A illustrates a plan view of a portion of an exemplary surgical instrument according to certain embodiments of the present disclosure.
FIG. 6B illustrates a plan view of a portion of an exemplary surgical instrument, according to certain embodiments of the present disclosure.

FIGS. 6A-6B illustrate side plan views of an exterior of probe 610 having different exemplary arrangements of opaque material 680 and translucent or transparent material 682 to modify the propagation of illumination light through distal portion 614 and proximal portion 612 of probe 610. Opaque material 680 refers to any suitable material, layer, device, or mechanism for reducing or preventing transmission of illumination light therethrough. For example, opaque material 680 may refer to areas of probe 610 having a higher refractive index relative to other areas of probe 610. In certain examples, opaque material 680 refers to opaque or semi-opaque portions of probe 610 through which reduced or no illumination light may pass. In other examples, opaque material 680 refers to an opaque or semi-opaque film or layer applied to an exterior or interior surface of probe 610. In still other examples, opaque material 680 refers to metal, e.g., stainless steel or other suitable alloy, portions of probe 610. In any form, opaque material 680 may be disposed in any suitable arrangement along a length L of probe 610 to provide optimal illumination of an intraocular space and reduce glare for a user of a surgical instrument caused by the illumination light.

In one exemplary embodiment depicted in FIG. 6A, opaque material 680 substantially forms or surrounds proximal portion 612 and distal portion 614 of probe 610, but for translucent or transparent portion 682 adjacent to ports 622. Translucent or transparent portion 682 begins proximal to ports 622 and terminates at distal tip 616. As a result, the transmission of illumination light from the one or more optical fibers within probe 610 to the surrounding environment is substantially reduced or prevented along a majority of length L covered by opaque material 680 that is proximal relative to translucent or transparent portion 682. Rather, a majority of illumination light emitted from probe 610 in FIG. 6A may be propagated radially outward 360° from translucent or transparent portion 382 near distal tip 616. Accordingly, illumination during use of probe 610 may be limited to an area adjacent to the surgical site (e.g., the trabecular meshwork) in which tissue fibers are laser-ablated during glaucoma surgery, as well as to an area adjacent to ports 622 through which viscoelastic or other fluids may be injected, thus providing improved visibility with reduced glare for a user thereof.

FIG. 6B depicts another exemplary arrangement of opaque material 680 and translucent or transparent material 682 of probe 610. In FIG. 6B, distal portion 614 of probe 610 is substantially formed of translucent or transparent material 682 but for an area of opaque material 680 at distal tip 616. During, e.g., goniotomy, distal tip 616 of probe 610 is often placed in close proximity to or in contact with the trabecular meshwork or surrounding tissues, and excess illumination emitted radially outward near distal tip 616 may cause unwanted damage to adjacent tissues. Thus, utilizing the material arrangement FIG. 6B prevents radially outward transmission of illumination light near distal tip 616, which may reduce or eliminate unwanted damage to tissues adjacent the surgical site.

Figures 7A, 7B:
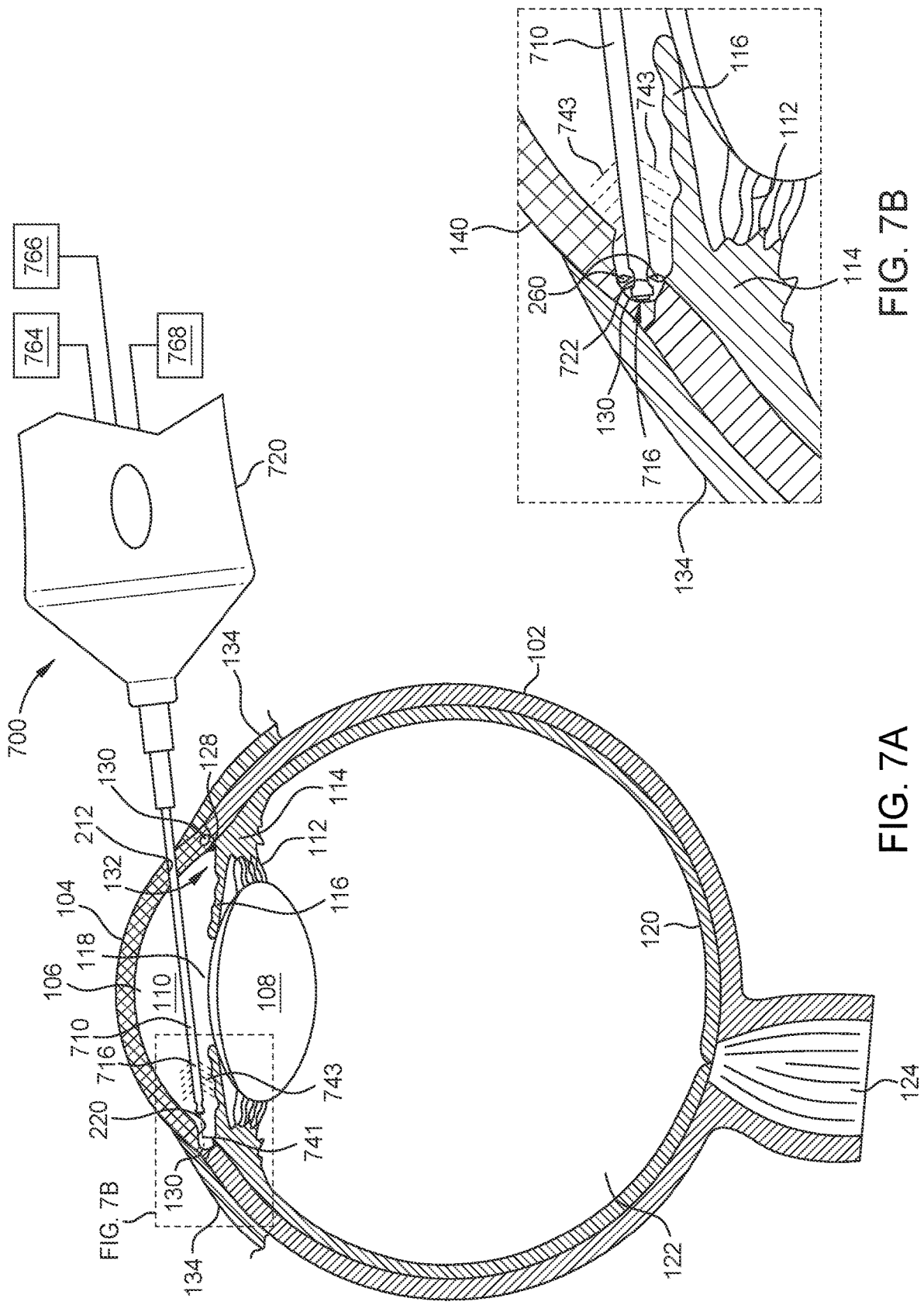
FIG. 7A illustrates a portion of an exemplary surgical instrument disposed within an eye of a patient during a surgical procedure, according to certain embodiments of the present disclosure.
FIG. 7B illustrates an enlarged cross-sectional view of the portion of the exemplary surgical instrument of FIG. 7A disposed within an eye of a patient during a surgical procedure, according to certain embodiments of the present disclosure.

FIGS. 7A-7B illustrate side sectional views of an interior anatomy of eye 100 during the performance of glaucoma surgery, e.g., a goniotomy procedure to eliminate an obstructed trabecular meshwork, using surgical instrument 700 having base unit 720 and probe 710. Probe 710 is representative of probes 310 and 610 above, either of which may be utilized as described herein. As shown in FIG. 7A, probe 710 is inserted into anterior chamber 106 of eye 100 through small, self-sealing incision 212 made in cornea 104 with, e.g., a surgical blade or the like. Distal tip 716 of probe 710 is advanced through anterior chamber 106 until it contacts or is substantially adjacent to trabecular meshwork 128 at iridocorneal angle 132. A user, e.g., a surgeon, may then activate laser light source 764 coupled to an optical fiber (not shown) disposed within surgical instrument 700, causing laser light 741 to be propagated within the optical fiber and emitted axially therefrom through a window (not shown) at distal tip 716 of probe 710. In certain embodiments, laser light source 764 is activated by the surgeon pressing upon a foot pedal (not shown) in wired or wireless communication with a surgical console driving laser light source 764. For example, laser light source 764 may be activated by the surgeon pressing the foot pedal to a first position.

In FIG. 7A, laser light 741 propagated by surgical instrument 700 disrupts, e.g., trabecular meshwork 128, forming fistula 220 therethrough. As described above, fistula 220 enables improved outflow of aqueous humor 110 from anterior chamber 106 to reduce or relieve intraocular pressure within eye 100, which may be caused by an obstruction of trabecular meshwork 128. In certain examples, a plurality of fistulas 220 are formed through trabecular meshwork 128 with surgical instrument 700 around a circumference of iridocorneal angle 132 to further increase a rate of outflow of aqueous humor 110. Aqueous humor 110 flows into Schlemm's canal 130, which facilitates gradual absorption of aqueous humor 110 into the patient's circulatory system. In certain embodiments, aqueous humor 110 may further flow from Schlemm's canal 130 into an artificially created reservoir under conjunctiva 134 called a bleb (not shown).

Simultaneously or sequentially with the propagation of laser light 741, the surgeon may activate illumination light source 766 coupled to the same or different optical fiber as laser light source 764, thereby causing illumination light 743 to be propagated within the corresponding optical fiber and emitted axially or laterally from probe 710. In certain examples, illumination light source 766 is activated prior to insertion of probe 710 into anterior chamber 106, or as distal tip 716 is advanced through anterior chamber 106 toward trabecular meshwork 128. In certain examples, illumination light source 766 is activated once distal tip 716 contacts or is substantially adjacent to trabecular meshwork 128. The propagation of illumination light 743 during the procedure enables improved visualization of the surgical site during the surgical procedure, e.g., trabecular meshwork 128 and fistula 220, as compared to, e.g., an external illumination provided by ophthalmic operating microscope. In certain embodiments, illumination light source 766 may be activated by the surgeon pressing upon the same foot pedal controlling laser light source 764. For example, illumination light source 766 may be activated by the surgeon pressing the foot pedal to a second position different from the first position for activating laser light source 764.

In the enlarged illustration of FIG. 7B, after formation of fistula 220, laser light source 764 is inactivated and distal tip 716 of probe 710 is advanced into fistula 220, or in close proximity thereto. The surgeon may then activate fluid source 768 coupled to probe 710, causing viscoelastic 260 to be flowed through an interior lumen (not shown) of probe 710 and injected laterally from ports 722 near distal tip 716 into fistula 220 (and thus, within trabecular meshwork 128 and/or Schlemm's canal 130). Viscoelastic 260 may be injected from probe 710 in opposite directions therefrom by, e.g., two ports 722 disposed on opposing sides of probe 710. In certain examples, the surgeon may rotate probe 310 to alter radial direction(s) of viscoelastic injection 260 from ports 722, and may further advance or pull back probe 710 through fistula 220 to distribute viscoelastic 260 within fistula 220 as desired. Injection of viscoelastic 260 within trabecular meshwork 128 and/or Schlemm's canal 130 facilitates engorgement and maintenance of fistula 220 after performance of glaucoma surgery, and may also preserve the integrity of anterior chamber 106.

In certain embodiments, injection of viscoelastic 260 from fluid source 768 is activated by the surgeon pressing the same foot pedal controlling laser light source 764 and illumination light source 766. For example, fluid source 768 may be activated upon pressing the foot pedal to a third position different than the first and second positions. In certain embodiments, the third position may include a range of positions of the foot pedal, the range of positions corresponding to different flow rates for fluid source 768 and thus, enabling different injection rates of viscoelastic 260. After injection of viscoelastic 260 into fistula 220, probe 710 may be removed from eye 100.

In summary, embodiments of the present disclosure include devices and structures for performing glaucoma-related surgery. In particular, the surgical instruments described above combine the functions of laser ablation, intraocular illumination, and viscoelastic injection, thus enabling more efficient performance of, e.g., goniotomy, trabeculotomy, and trabeculectomy. Utilization of a laser probe allows tissue fibers of the trabecular meshwork and surrounding tissues to be easily disrupted, while the inclusion of fluid ports on the probe enables fluid injection near the surgical site without removal of the laser probe or need for a secondary injection device. Furthermore, propagation of illumination light through the laser probe facilitates diffuse intraocular illumination for improved visibility during a produce. Accordingly, the described embodiments enable the performance of more efficient, less invasive, and safer glaucoma-related surgical procedures.

Although glaucoma surgery is discussed as an example of a surgical procedure that may benefit from the described embodiments, the advantages of the surgical devices and systems described herein may benefit other surgical procedures as well.

While the foregoing is directed to embodiments of the present disclosure, other and further embodiments of the disclosure may be devised without departing from the basic scope thereof, and the scope thereof is determined by the claims that follow.

Example Embodiments

Embodiment 1: A surgical instrument for an ophthalmic procedure, comprising: a handle; a probe coupled to the handle, the probe comprising: a tube; an optically clear or transparent window disposed within a distal end of the tube; and one or more optical fibers extending at least partially through the tube, the one or more optical fibers configured to transmit a laser light for irradiating an area proximate to the window for ablation of a trabecular meshwork of a patient, the one or more optical fibers further transmitting an illumination light for illumination of an intraocular space of the patient; and a first port and a second port formed proximate to the distal end of the tube for injecting a viscoelastic fluid into the ablated trabecular meshwork.

Embodiment 2: The surgical instrument of embodiment 1, wherein the illumination light is focused on a cladding of one of the one or more optical fibers.

Embodiment 3: The surgical instrument of embodiment 1, wherein the illumination light is focused on a core of one of the one or more optical fibers.

Embodiment 4: The surgical instrument of embodiment 3, wherein the illumination light is also focused on a cladding of the one of the one or more optical fibers.

Embodiment 5: The surgical instrument of embodiment 1, wherein the laser light and the illumination light are simultaneously projected through the one or more optical fibers.

Embodiment 6: The surgical instrument of embodiment 1, wherein the laser light and the illumination light are sequentially pulsed through the one or more optical fibers.

Embodiment 7: The surgical instrument of embodiment 1, wherein the window comprises a lens.

Embodiment 8: The surgical instrument of embodiment 1, wherein the window comprises at least one of sapphire, fused silica, glass, or ceramic material.

Embodiment 9: The surgical instrument of embodiment 1, further comprising a lens housed in the tube, the lens positioned between the one or more optical fibers and the window.

Embodiment 10: The surgical instrument of embodiment 1, wherein the tube has a gauge of 25 or less.

What is claimed is:

1. A surgical instrument for an ophthalmic procedure, comprising:
    a laser light source;
    an illumination light source;
    a handle; and
    a probe coupled to the handle, the probe further coupled to the laser light source and to the illumination light source, the probe comprising:
        one or more optical fibers configured to transmit a laser light from the laser light source for ablation of a trabecular meshwork of a patient, the one or more optical fibers further configured to transmit an illumination light from the illumination light source for illumination of an intraocular space of the patient;
        a tube surrounding the one or more optical fibers, the tube comprising a portion that is translucent or transparent for facilitating transmission of the illuminated light emitted radially outward from the one or more optical fibers; and
        a first port formed proximate to a distal end of the tube for injecting a viscoelastic fluid into the ablated trabecular meshwork.

2. The surgical instrument of claim 1, wherein the one or more optical fibers comprise a single optical fiber configured to project the laser light and the illumination light.

3. The surgical instrument of claim 2, wherein the laser light source is configured to focus the laser light on a core of the single optical fiber and the illumination light source is configured to focus the illumination light on a cladding of the single optical fiber.

4. The surgical instrument of claim 3, wherein the illumination light source is configured to focus the illumination light on the core of the single optical fiber.

5. The surgical instrument of claim 1, wherein the one or more optical fibers comprise a first optical fiber configured to project the laser light and a second optical fiber configured to project the illumination light.

6. The surgical instrument of claim 1, wherein the laser light source is configured to provide a pulsed laser light.

7. The surgical instrument of claim 6, wherein the laser light source is configured to provide a picosecond laser light.

8. The surgical instrument of claim 6, wherein the laser light source is configured to provide a femtosecond laser light.

9. The surgical instrument of claim 1, wherein the laser light source is configured to provide a continuous laser light.

10. The surgical instrument of claim 1, wherein the illumination light source is configured to provide a pulsed illumination light.

11. The surgical instrument of claim 1, wherein the one or more optical fibers are configured to project the laser light and the illumination light axially.

12. The surgical instrument of claim 1, wherein the one or more optical fibers are disposed within the tube such that an injection space circumferentially surrounds the one or more optical fibers, and wherein the one or more optical fibers extend distally past the first port.

13. The surgical instrument of claim 12, wherein the injection space facilitates flow of the viscoelastic fluid from a fluid source into the tube and through the first port.

14. The surgical instrument of claim 1, further comprising a second port formed proximate to the distal end of the tube and opposite the first port, the second port for injecting the viscoelastic fluid from a fluid source into the ablated trabecular meshwork in a direction opposite of the viscoelastic fluid injected from the first port.

15. The surgical instrument of claim 1, wherein the translucent or transparent portion of the tube extends along a majority of the length of the tube, and wherein the tube further comprises an opaque portion distal to the translucent or transparent portion.

\* \* \* \* \*